United States Patent
Ramesh et al.

(10) Patent No.: US 10,687,697 B2
(45) Date of Patent: Jun. 23, 2020

(54) ENDOSCOPIC LIGHT SOURCE AND IMAGING SYSTEM

(71) Applicant: Stryker Corporation, Kalamazoo, MI (US)

(72) Inventors: Ajay Ramesh, San Jose, CA (US); Perry Hu, San Jose, CA (US); Harman Singh, Fremont, CA (US); Chien Mien Pang, San Jose, CA (US); Vasudev Nambakam, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 39 days.

(21) Appl. No.: 14/775,347

(22) PCT Filed: Mar. 14, 2014

(86) PCT No.: PCT/US2014/027700
§ 371 (c)(1),
(2) Date: Sep. 11, 2015

(87) PCT Pub. No.: WO2014/152757
PCT Pub. Date: Sep. 25, 2014

(65) Prior Publication Data
US 2016/0022126 A1    Jan. 28, 2016

Related U.S. Application Data

(60) Provisional application No. 61/792,165, filed on Mar. 15, 2013.

(51) Int. Cl.
*A61B 1/06* (2006.01)
*A61B 1/07* (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
CPC ..... A61B 1/0638; A61B 1/07; A61B 1/00045; A61B 1/045; A61B 1/00006;
(Continued)

(56) References Cited

U.S. PATENT DOCUMENTS

| | | |
|---|---|---|
| 4,538,062 A | 8/1985 | Shishido |
| 5,084,612 A | 1/1992 | Iwasaki et al. |

(Continued)

FOREIGN PATENT DOCUMENTS

| | | |
|---|---|---|
| CN | 1870932 A | 11/2006 |
| CN | 101295102 A | 10/2008 |

(Continued)

OTHER PUBLICATIONS

International Search Report issued in PCT/US2014/027700 dated Nov. 3, 2014 (6 pages).

(Continued)

*Primary Examiner* — Alexandra L Newton
*Assistant Examiner* — Genja M Frankert
(74) *Attorney, Agent, or Firm* — Morrison & Foerster LLP

(57) ABSTRACT

An endoscopic system having a light source that can operate in two modes is provided. The first mode provides a white light to an endoscope to transmit the light to a surgical site or other object, the reflection of which can be received by the endoscope and for the process. The second mode of the light source provides infrared excitation light and light in the blue and green wavelength spectra to an endoscope to transmit the light to an object such as a surgical site. The blue and green reflected light, as well as light from excitation mark- (Continued)

ers, which is an infrared light at a different wavelength than the excitation infrared light, is received by the endoscope and further processed.

13 Claims, 10 Drawing Sheets

(51) Int. Cl.
*A61B 1/045* (2006.01)
*A61B 1/00* (2006.01)
*A61B 1/04* (2006.01)
*H04N 9/73* (2006.01)
*G01N 21/64* (2006.01)
*H04N 5/33* (2006.01)
*H04N 5/225* (2006.01)

(52) U.S. Cl.
CPC ...... *A61B 1/00045* (2013.01); *A61B 1/00057* (2013.01); *A61B 1/00186* (2013.01); *A61B 1/043* (2013.01); *A61B 1/045* (2013.01); *A61B 1/063* (2013.01); *A61B 1/0646* (2013.01); *A61B 1/0669* (2013.01); *A61B 1/0684* (2013.01); *A61B 1/07* (2013.01); *G01N 21/6428* (2013.01); *G01N 21/6456* (2013.01); *H04N 5/332* (2013.01); *H04N 9/73* (2013.01); *A61B 1/042* (2013.01); *G01N 2021/6439* (2013.01); *G01N 2021/6484* (2013.01); *H04N 2005/2255* (2013.01)

(58) Field of Classification Search
CPC ... A61B 1/00057; A61B 1/063; A61B 1/0684; A61B 1/0646; A61B 1/0669; A61B 1/00009; H04N 5/332; H04N 9/73; G01N 21/6428; G01N 21/6456
See application file for complete search history.

(56) References Cited

U.S. PATENT DOCUMENTS

| | | |
|---|---|---|
| 5,132,526 A | 7/1992 | Iwasaki |
| 5,269,289 A | 12/1993 | Takehana et al. |
| 5,636,259 A | 6/1997 | Khutoryansky et al. |
| 5,717,605 A | 2/1998 | Komiya et al. |
| 5,842,765 A | 12/1998 | Cassarly et al. |
| 5,917,883 A | 6/1999 | Khutoryansky et al. |
| 5,957,834 A | 9/1999 | Mochida |
| 6,040,940 A | 3/2000 | Kawasaki |
| 6,193,401 B1 | 2/2001 | Girkin et al. |
| 6,195,154 B1 | 2/2001 | Imai |
| 6,293,911 B1 | 9/2001 | Imaizumi |
| 6,485,414 B1 | 11/2002 | Neuberger |
| 6,549,239 B1 | 4/2003 | Tao |
| 6,563,632 B1 | 5/2003 | Schoeppe et al. |
| 6,663,560 B2 | 12/2003 | MacAulay et al. |
| 6,730,019 B2 | 5/2004 | Irion |
| 6,876,494 B2 | 4/2005 | Ishikawa et al. |
| 6,924,490 B2 | 8/2005 | Natori |
| 7,015,444 B2 | 3/2006 | Kawano et al. |
| 7,016,053 B2 | 3/2006 | Moriuchi et al. |
| 7,176,428 B2 | 2/2007 | Kawano et al. |
| 7,223,986 B2 | 5/2007 | Natori |
| 7,239,384 B2 | 7/2007 | Kawano |
| 7,258,663 B2 | 8/2007 | Doguchi et al. |
| 7,268,938 B2 | 9/2007 | Kawano et al. |
| 7,304,789 B2 | 12/2007 | Hirata et al. |
| 7,448,995 B2 | 11/2008 | Wiklof et al. |
| 7,583,389 B2 | 9/2009 | Neal et al. |
| 7,609,440 B2 | 10/2009 | Tanikawa et al. |
| 7,616,330 B2 | 11/2009 | Neal et al. |
| 7,623,251 B2 | 11/2009 | Neal et al. |
| 7,661,862 B2 | 2/2010 | Lee et al. |
| 7,865,230 B1* | 1/2011 | Sevick-Muraca .... A61B 5/0091 600/473 |
| 8,408,704 B2 | 4/2013 | Tomidokoro et al. |
| 8,892,190 B2 | 11/2014 | Docherty et al. |
| 2002/0013531 A1* | 1/2002 | Hayashi ............ A61K 49/0034 600/476 |
| 2002/0014595 A1 | 2/2002 | Sendai et al. |
| 2002/0043636 A1 | 4/2002 | Kimura |
| 2002/0101643 A1 | 8/2002 | Kobayashi |
| 2002/0120181 A1 | 8/2002 | Irion |
| 2002/0168096 A1 | 11/2002 | Hakamata et al. |
| 2003/0007087 A1 | 1/2003 | Hakamata et al. |
| 2003/0042493 A1 | 3/2003 | Kazakevich |
| 2003/0067645 A1 | 4/2003 | Ibsen et al. |
| 2003/0147254 A1 | 8/2003 | Yoneda et al. |
| 2003/0169431 A1 | 9/2003 | Moriuchi et al. |
| 2003/0184661 A1 | 10/2003 | Yubata et al. |
| 2003/0202090 A1 | 10/2003 | Ota et al. |
| 2004/0061673 A1 | 4/2004 | Ishikawa et al. |
| 2004/0105095 A1 | 6/2004 | Stobrawa et al. |
| 2004/0105482 A1 | 6/2004 | Sugiyama et al. |
| 2004/0147806 A1 | 7/2004 | Adler |
| 2004/0186351 A1* | 9/2004 | Imaizumi ........... A61B 1/00009 600/160 |
| 2004/0228373 A1 | 11/2004 | Tatsuno et al. |
| 2005/0020926 A1 | 1/2005 | Wiklof et al. |
| 2005/0099824 A1 | 5/2005 | Dowling et al. |
| 2005/0187441 A1 | 8/2005 | Kawasaki et al. |
| 2005/0200947 A1 | 9/2005 | Hirata et al. |
| 2005/0203423 A1 | 9/2005 | Zeng et al. |
| 2005/0211872 A1 | 9/2005 | Kawano et al. |
| 2005/0224692 A1 | 10/2005 | Tsuchiya et al. |
| 2005/0228231 A1 | 10/2005 | MacKinnon et al. |
| 2005/0237416 A1* | 10/2005 | Hasegawa ........... H04N 5/2254 348/335 |
| 2005/0237604 A1 | 10/2005 | Kawano et al. |
| 2005/0251230 A1 | 11/2005 | MacKinnon et al. |
| 2005/0253056 A1 | 11/2005 | Nakata |
| 2005/0270641 A1 | 12/2005 | Hirata et al. |
| 2005/0276553 A1 | 12/2005 | Kazakevich |
| 2005/0279950 A1 | 12/2005 | Kawano et al. |
| 2006/0009682 A1 | 1/2006 | Nagasawa et al. |
| 2006/0017920 A1 | 1/2006 | Tsuchiya et al. |
| 2006/0103922 A1 | 5/2006 | Tsuyuki |
| 2006/0146125 A1 | 7/2006 | Yamada |
| 2006/0175546 A1 | 8/2006 | Asai |
| 2006/0187499 A1 | 8/2006 | Natori et al. |
| 2007/0028918 A1 | 2/2007 | Tsuyuki et al. |
| 2007/0051869 A1 | 3/2007 | Knebel |
| 2007/0091425 A1 | 4/2007 | Kawano |
| 2007/0097369 A1 | 5/2007 | Shimada |
| 2007/0100241 A1 | 5/2007 | Adler |
| 2007/0104417 A1 | 5/2007 | Tanaka et al. |
| 2007/0120070 A1 | 5/2007 | Kawano et al. |
| 2007/0153367 A1 | 7/2007 | Kawasaki |
| 2007/0159682 A1 | 7/2007 | Tanaka et al. |
| 2007/0188707 A1 | 8/2007 | Nanjo |
| 2007/0213588 A1 | 9/2007 | Morishita et al. |
| 2007/0213593 A1 | 9/2007 | Nakaoka |
| 2007/0236701 A1 | 10/2007 | Neal et al. |
| 2007/0236702 A1 | 10/2007 | Neal et al. |
| 2007/0236703 A1 | 10/2007 | Neal et al. |
| 2007/0270652 A1 | 11/2007 | Morishita et al. |
| 2007/0274649 A1 | 11/2007 | Takahashi et al. |
| 2007/0299309 A1 | 12/2007 | Seibel et al. |
| 2008/0039695 A1 | 2/2008 | Takaoka et al. |
| 2008/0043244 A1 | 2/2008 | Hatori et al. |
| 2008/0137328 A1 | 6/2008 | Lee et al. |
| 2008/0186388 A1 | 8/2008 | Yamagata et al. |
| 2008/0198448 A1 | 8/2008 | Ganser et al. |
| 2008/0225388 A1 | 9/2008 | Hirata |
| 2008/0232131 A1 | 9/2008 | Suda |
| 2008/0239070 A1* | 10/2008 | Westwick ............ A61B 1/045 348/68 |
| 2008/0246920 A1 | 10/2008 | Buczek et al. |
| 2008/0252900 A1 | 10/2008 | Hatori |
| 2008/0255458 A1* | 10/2008 | Dunki-Jacobs ...... A61B 5/0071 600/476 |
| 2008/0283770 A1 | 11/2008 | Takahashi |

(56) References Cited

U.S. PATENT DOCUMENTS

| | | | |
|---|---|---|---|
| 2009/0021739 A1* | 1/2009 | Tsujita | A61B 1/00163 356/407 |
| 2009/0032732 A1 | 2/2009 | Konishi et al. | |
| 2009/0067042 A1 | 3/2009 | Tanikawa et al. | |
| 2009/0073553 A1 | 3/2009 | Hirata | |
| 2009/0201577 A1 | 8/2009 | LaPlante et al. | |
| 2009/0203994 A1* | 8/2009 | Mangat | A61B 5/0261 600/433 |
| 2009/0244521 A1 | 10/2009 | Yazdanfar et al. | |
| 2009/0251704 A1 | 10/2009 | Masuda | |
| 2009/0289200 A1* | 11/2009 | Ishii | A61B 1/00009 250/459.1 |
| 2009/0303317 A1* | 12/2009 | Tesar | C03C 17/3417 348/65 |
| 2010/0312122 A1* | 12/2010 | Yazdanfar | A61K 49/0021 600/476 |
| 2011/0019032 A1* | 1/2011 | Pinsky | G06T 5/009 348/238 |
| 2011/0042580 A1* | 2/2011 | Wilson | G01N 21/6456 250/458.1 |
| 2011/0063427 A1* | 3/2011 | Fengler | A61B 1/00186 348/65 |
| 2011/0118575 A1* | 5/2011 | Lloyd | A61B 5/0059 600/328 |
| 2011/0208004 A1* | 8/2011 | Feingold | A61B 1/045 600/178 |
| 2011/0270057 A1* | 11/2011 | Pascal | A61B 1/041 600/317 |
| 2011/0270092 A1* | 11/2011 | Kang | A61B 5/0071 600/476 |
| 2012/0004508 A1* | 1/2012 | McDowall | A61B 1/00186 600/178 |
| 2012/0004557 A1* | 1/2012 | McDowall | A61B 1/00186 600/476 |
| 2012/0016230 A1* | 1/2012 | Kishima | A61B 1/00186 600/425 |
| 2012/0230024 A1* | 9/2012 | Moore | A61B 1/063 362/231 |
| 2012/0248333 A1 | 10/2012 | Fallert et al. | |
| 2012/0257030 A1 | 10/2012 | Lim et al. | |
| 2013/0041226 A1* | 2/2013 | McDowall | A61B 1/00009 600/166 |
| 2013/0070071 A1* | 3/2013 | Peltie | A61B 1/05 348/68 |
| 2013/0300836 A1* | 11/2013 | Zhao | H04N 9/045 348/46 |
| 2014/0350395 A1* | 11/2014 | Shachaf | G06T 7/0012 29/401.1 |
| 2015/0112192 A1 | 4/2015 | Docherty et al. | |
| 2015/0112193 A1 | 4/2015 | Docherty et al. | |
| 2015/0148626 A1* | 5/2015 | Sella-Tavor | A61B 5/0071 600/314 |

FOREIGN PATENT DOCUMENTS

| | | |
|---|---|---|
| EP | 1 930 751 A2 | 6/2008 |
| JP | 54-10237 Y2 | 6/1975 |
| JP | 7-67832 A | 3/1995 |
| JP | 7-275192 A | 10/1995 |
| JP | 11-253384 A | 9/1999 |
| JP | 2001-224015 A | 8/2001 |
| JP | 2006-87764 A | 4/2006 |
| WO | WO 2005/000110 A2 | 1/2005 |
| WO | WO 2010/059197 A2 | 5/2010 |

OTHER PUBLICATIONS

Written Opinion of the International Searching Authority issued in PCT/US2014/027700 dated Nov. 3, 2014 (7 pages).

European Office Action dated Apr. 1, 2019 for EP Application No. 14724563.3 filed Oct. 14, 2015, 9 pages.

International Preliminary Report on Patentability dated Sep. 24, 2015 for PCT Application No. PCT/US2014/027700 filed on Mar. 14, 2014, 9 pages.

European Office Action dated Feb. 13, 2020 for EP Application No. 14724563.3 filed Oct. 14, 2015, 5 pages.

* cited by examiner

ENDOSCOPIC LIGHT SOURCE AND IMAGING SYSTEM

CROSS REFERENCE TO RELATED APPLICATIONS

This is the National Stage of International Application No. PCT/US2014/027700, filed Mar. 14, 2014, which claims the priority of U.S. Provisional Application No. 61/792,165, filed Mar. 15, 2013.

BACKGROUND OF THE INVENTION

The present invention relates generally to a solid state system for providing illumination from an external light source through an instrument to an object, such as a patient surgical site. The external light source includes components for providing light in the visible spectrum as well as light in the infrared spectrum.

Endoscopic systems are used to inspect regions within a body during surgery. Endoscopic systems typically include an endoscope, a light source, and an imaging device such as a camera head. Typically, an endoscope includes a rigid or flexible elongated insertion tube equipped with a set of optical fibers that extend from a proximal handle through the endoscope body to a distal viewing tip. An external light source provides light to the optic fibers via a cable that attaches to a post or other structure on the endoscope. The endoscope also receives images and transmits them to the imaging device for providing a image to a monitor or other display apparatus for viewing by a surgeon.

In one commercial embodiment, an endoscopic system includes a solid state light source that generates white light which is conveyed to a distal end of the endoscope via a light guide. The light guide includes multiple fibers and is connected between an output connector of the light source and a light post of the endoscope. The white light illuminates a working area at the distal end of the endoscope. The camera, connected to a handle of the endoscope, generates video signals representative of images at the working area for display on a video monitor.

The light source includes an optical system and a lens array used to collimate light from an LED array. A focusing lens focuses the light onto the light guide. The lenses collect light emitted by LEDs. The lenses may be single lenses, such as single or double aspherics, compound lenses, radiant index type lenses, or combinations of each of these. Other arrangements have lens arrays that are implemented as part of an LED array by adhesion, fusion, or other means. Some arrangements have a rectangular-shaped LED and lens array.

The focal length of the lens and the diameter of the lenses are chosen on the order of a few millimeters. The actual values are selected based on the size of the LED emitting surface which determines the field of view of the lens.

The collected light from the lens array travels to a focusing lens. The focusing lens projects the image of each LED light emitting surface onto an entrance face of the light guide. The image is magnified so that the size is approximately equal to the size of the entrance face of the light guide. The light guide transports the light to the endoscope. The light passes through the endoscope to illuminate a surgical site. Light is reflected off of the surgical site which is received by the endoscope and transmitted to the camera head. The camera head provides images of the surgical site for display on the monitor.

Another endoscopic system that has been designed is described in commonly-owned PCT Application No. WO 2010/059197 A2, which is incorporated in its entirety by reference.

The above-described endoscopic systems do not concern themselves with the ability of excitation of fluorescent markers in an object, such as a body part at a surgical site. While there are systems on the market that do provide excitation light for fluorescent markers, these systems typically use multiple light sources and multiple components to transmit infrared light to the surgical site, and multiple components to separate the fluorescent light emitted by the fluorescent markers. The present invention is a solution to those problems.

One embodiment of the present invention includes a single light source which is capable of providing white light, i.e. light in the visible spectrum, and providing infrared light capable of exciting fluorescent markers at a surgical site through an endoscope. The endoscope is also capable of receiving reflected light from the surgical site and fluorescent light emitted from the fluorescent markers.

Another embodiment of the invention employs a light source to provide light in the red, blue, green, and infrared wavelength spectra to an endoscope which transports the light to a surgical site. Reflected light and fluorescent light from fluorescent markers at the surgical site are then transmitted through the endoscope, through a notch filter, and then to a trichroic prism for separation into light in the infrared spectrum, light in the blue spectrum, and light in the green spectrum.

Other advantages, objects and/or purposes of the invention will be apparent to persons familiar with constructions of this general type upon reading the following specification and inspecting the accompanying drawings.

DETAILED DESCRIPTION

Figure 1:
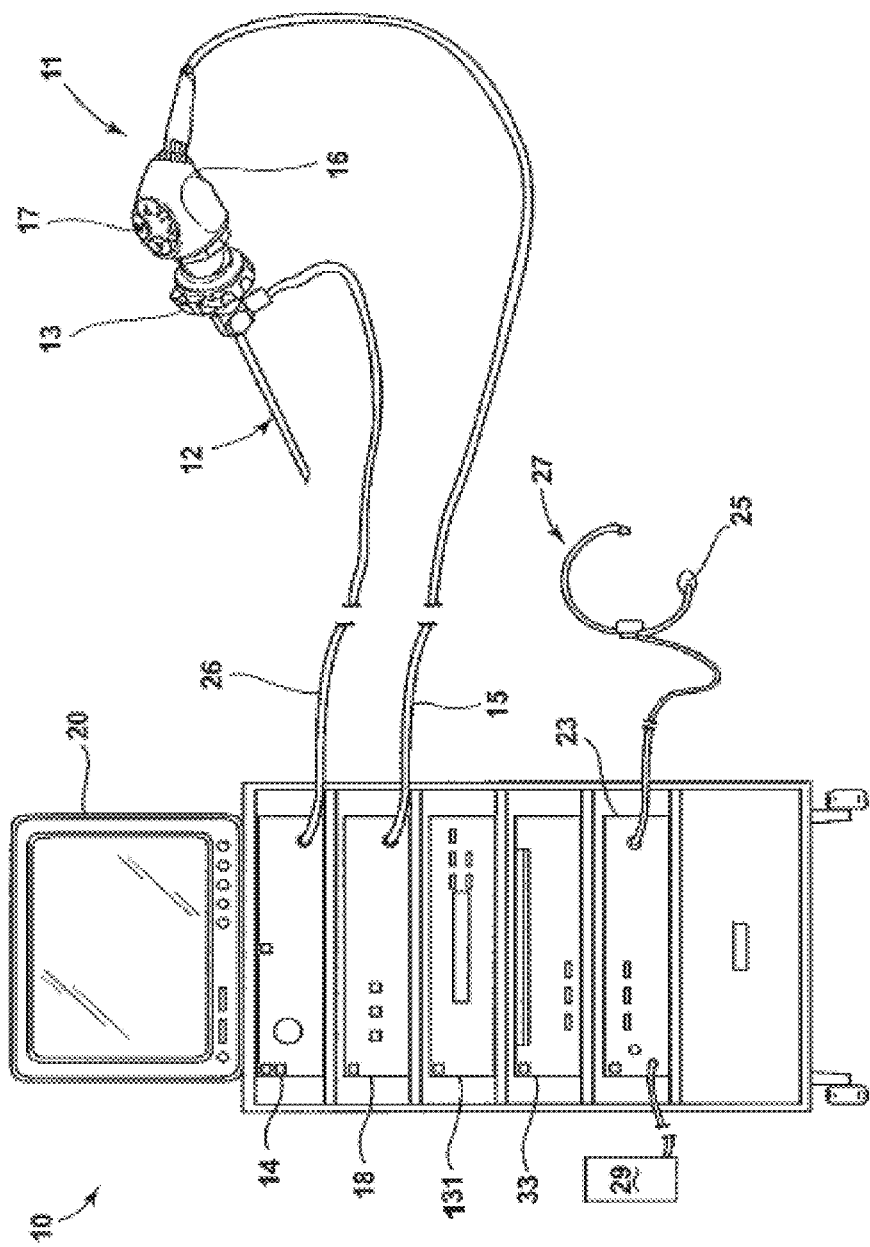
FIG. 1 is an illustration of an endoscopic camera arrangement which is an embodiment of the present invention.

Certain terminology will be used in the following description for convenience and reference only, and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the arrangement, and designated parts thereof. This terminology includes the words specifically mentioned, derivatives thereof, and words of similar import.

FIG. 1 shows an endoscopic camera arrangement 10, including a scope assembly 11 which may be utilized in endoscopic procedures. The scope assembly 11 incorporates an endoscope or scope 12 which is coupled to a camera head 16 by a coupler 13 located at the distal end of the camera head 16. Light is provided to the scope by a light source 14 via a light guide 26, such as a fiber optic cable. The camera head 16 is coupled to a camera control unit (CCU) 18 by an electrical cable 15. The CCU 18 is connected to, and communicates with, the light source 14. Operation of the camera 16 is controlled, in part, by the CCU 18. The cable 15 conveys video image data from the camera head 16 to the CCU 18 and conveys various control signals bi-directionally between the camera head 16 and the CCU 18. In one embodiment, the image data output by the camera head 16 is digital.

A control or switch arrangement 17 is provided on the camera head 16 and allows a user to manually control various functions of the arrangement 10. Voice commands are input into a microphone 25 mounted on a headset 27 worn by the surgeon and coupled to the voice-control unit 23. A hand-held control device 29, such as a tablet with a touch screen user interface or a PDA, may be coupled to the voice control unit 23 as a further control interface. In the illustrated embodiment, a recorder 131 and a printer 33 are also coupled to the CCU 18. Additional devices, such as an image capture and archiving device, may be included in the arrangement 10 and coupled to the CCU 18. Video image data acquired by the camera head 16 and processed by the CCU 18 is converted to images, which can be displayed on a monitor 20, recorded by recorder 131, and/or used to generate static images, hard copies of which can be produced by the printer 33.

Figure 1A:
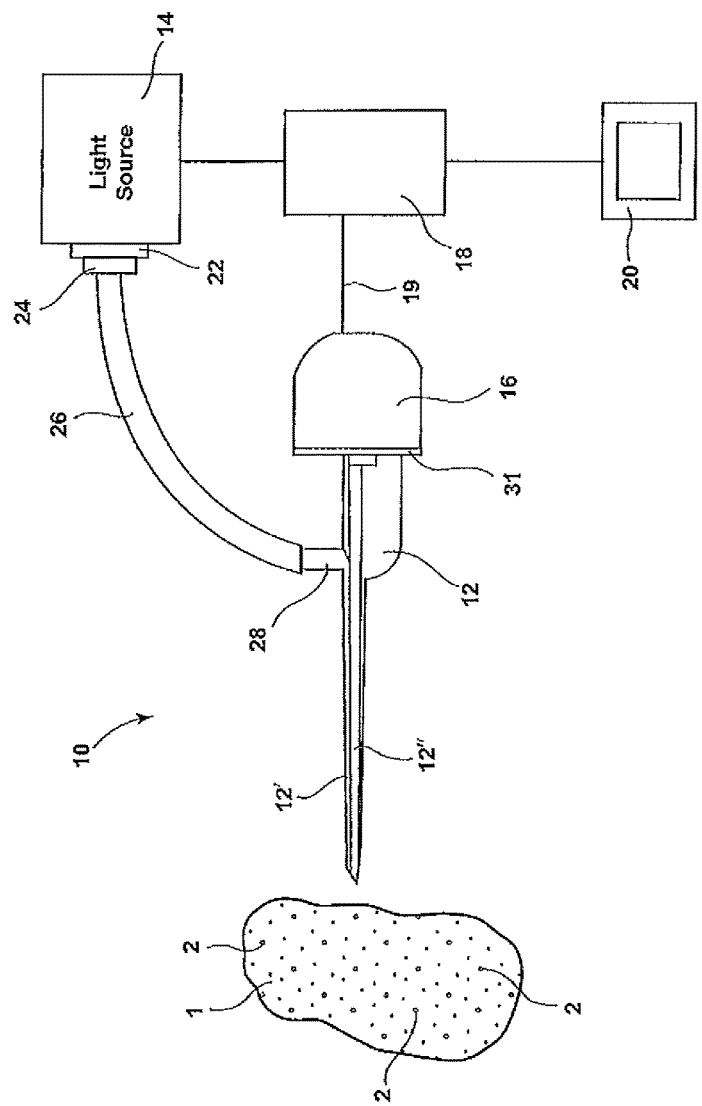
FIG. 1A is a diagram of a portion of the endoscopic camera arrangement of FIG. 1 and an object with fluorescent markers in it.

FIG. 1A shows an embodiment of part of the endoscopic system 10 used to illuminate and receive light from an object 1, such as a surgical site of a patient. The object 1 includes fluorescent markers 2 therein. The fluorescent markers 2 are preferably comprised of indocyanine green (ICG) which is an FDA-approved fluorescent dye for bile duct identification and sentinel lymph node (SLN) identification.

The light source 14 generates white light (a combination of red, green, and blue light) in a first mode, and infrared, blue, and green light in a second mode. In both modes, the light is transmitted to and through an optic lens system 22 which focuses light onto a light pipe 24. The light pipe 24 is preferably five millimeters in diameter and creates a homogeneous light, which is then transmitted to the fiber optic light guide 26. The light guide 26 includes multiple optic fibers and is connected to a light post 28, which is part of the endoscope 12. The endoscope 12 has an illumination pathway 12' and an optical channel pathway 12".

The endoscope 12 includes a notch filter 31, which allows at least 80% of infrared light in a wavelength range of 830 nm to 870 nm to pass therethrough and allows at least 80% of visible light in the wavelength range of 400 nm to 700 nm to pass therethrough, but blocks light having a wavelength of 808 nm. The notch filter 31 should have an optical density of OD5 or higher. Alternatively, the notch filter 31 can be located in the coupler 13.

Figure 2:
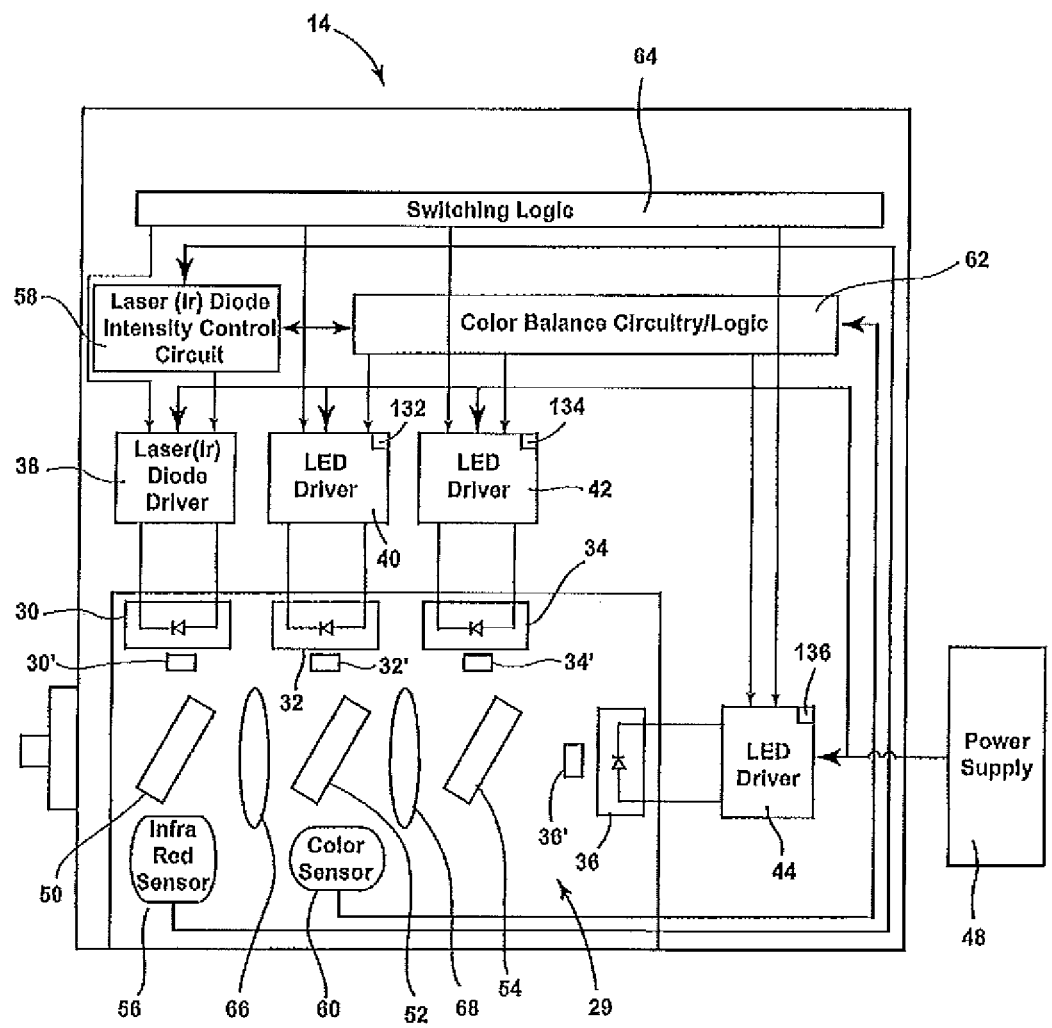
FIG. 2 is a block diagram of a light source of the endoscopic system of FIG. 1.

The basic components of the light source 14 are shown in FIG. 2. The light source 14 includes an LED and laser diode section 29, which has a laser diode 30, a first LED 32, a second LED 34, and a third LED 36. The laser diode 30 is preferably an infrared diode (denoted by the letters IR) which emits light having a wavelength in the range of about 805 nm to about 810 nm, and more preferably having a wavelength of about 808 nm. Preferably, the first LED 32 emits light in the blue wavelength spectrum, the second LED 34 emits light in the green wavelength spectrum, and the third LED 36 emits light in the red wavelength spectrum. The infrared laser diode 30 is activated by a laser diode driver 38, the first LED 32 is activated by a first LED driver 40, the second LED 34 is activated by a second LED driver 42, and the third LED 36 is activated by a third LED driver 44. The drivers 38, 40, 42, 44 are each powered by an external power supply 48.

Adjacent the laser diode 30 is a first optical component 30', used to spread the laser light. Adjacent the first LED 32 is a second optical component 32', adjacent the second LED 34 is a third optical component 34', and adjacent the third LED 36 is a fourth optical component 36'. The optical components 32', 34', 36' are for the purpose of decreasing the angles of the paths of the light emitted from the LEDs 32, 34, 36, respectively. The optical components 30', 32', 34', 36' may be any component that is capable of achieving the desired purpose, but preferably are lenses or light pipes.

Adjacent the first optical component 30' is a first dichroic filter 50, adjacent the second optical component 32' is a second dichroic filter 52, and adjacent both the third optical component 34' and the fourth optical component 36' is a third dichroic filter 54. The dichroic filters 50, 52, 54 are each designed to reflect certain light and allow passage of other light therethrough, as described in more detail below.

An infrared sensor 56 is positioned adjacent the first dichroic filter 50, at a location opposite the laser diode 30. The infrared sensor 56 detects the presence of infrared light, and when the presence of infrared light is detected, it provides a signal to a laser diode intensity control circuit 58. The laser diode intensity control circuit 58 is connected to the laser diode driver 38 and controls the intensity of the light emitted from the laser diode 30.

A color sensor 60 is positioned adjacent the second dichroic filter 52, at a location opposite the first LED 32. The color sensor 60 detects light in the visible light wavelength spectrum, and when visible light is detected, it provides a signal to a color balance circuit/logic device 62. The amount of visible light detected is used by the color balance circuit/logic device 62 to provide signals to the LED drivers 40, 42, 44 to adjust the intensity of one or more of the LEDs 32, 34, 36, such that the preferred balance of light in the visible spectrum is achieved.

A switching logic device 64 is provided which switches the light source 14 between the two modes. The first mode is a visible white light mode in which the laser diode 30 is off, the first LED 32 is on, the second LED 34 is on, and the third LED 36 is on. The second mode is an infrared excitation light and background light mode in which the laser diode 30 is on, the first LED 32 is on, the second LED 34 is on, and the third LED 36 is off. The second mode provides infrared light to the surgical site for excitation of fluorescent markers, and provides light in the blue and green visible wavelength spectrums for background light.

Figure 3:
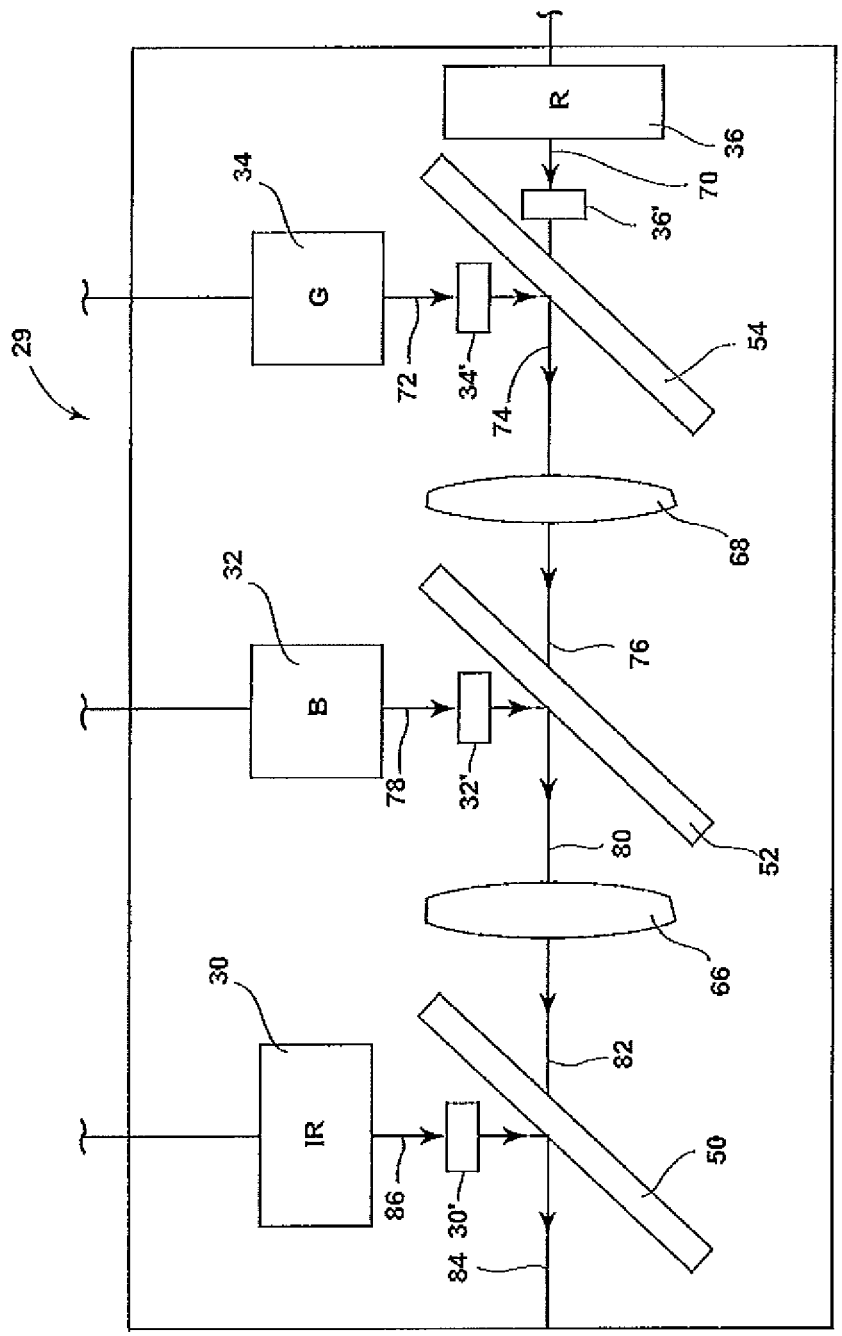
FIG. 3 is a diagrammatic view of an LED and laser diode portion of the light source of FIG. 2.

FIG. 3 shows a more detailed view of the LED and laser diode section 29. In this arrangement, the first dichroic filter 50 allows all visible light (i.e. light in the blue, green, and red wavelength spectra) to pass, while reflecting 808-nm infrared light. The second dichroic filter 52 allows light in the red and green wavelength spectra to pass while reflecting light in the blue wavelength spectrum. The third dichroic filter 54 allows light in the red wavelength spectrum to pass, while reflecting light in the green wavelength spectrum. A first optical lens 66 is located between the first dichroic filter 50 and the second dichroic filter 52, and is for focusing light received from the second dichroic filter 52 to be passed to the first dichroic filter 50. A second optical lens 68 is located between the second dichroic filter 52 and the third dichroic filter 54, and is for focusing light received from the third dichroic filter 54 to be passed to the second dichroic filter 52.

Figure 4A:
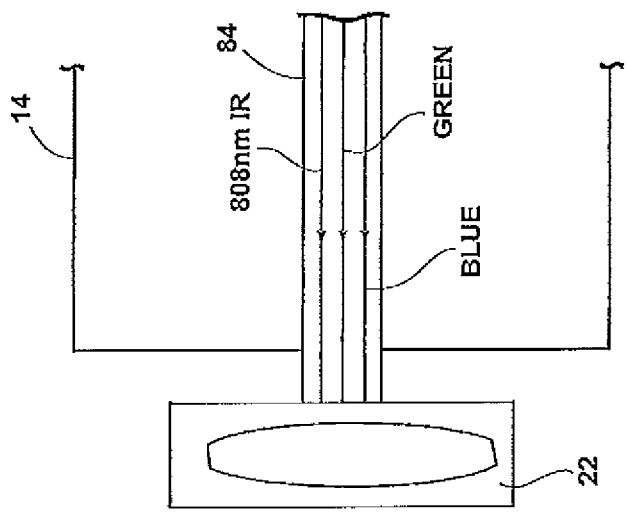
FIG. 4a is a diagrammatic view of a collimating lens receiving light of a first set of light wavelengths.

In operation in the first mode, power is not supplied to the laser diode driver 38, but is supplied to the first LED driver 40, the second LED driver 42, and the third LED driver 44. Thus, in this mode, no light is provided by the laser diode 30, but light is provided by the first LED 32, the second LED 34, and the third LED 36. Light in the red wavelength spectrum is emitted from the third LED 36 in the direction of the pathway 70 toward the fourth optical component 36' and the third dichroic filter 54, as shown in FIG. 3. Light in the green wavelength spectrum is emitted from the second LED 34 in the direction of the pathway 72 toward the third optical component 34' and the third dichroic filter 54. Because the third dichroic filter 54 allows red light to pass and reflects green light, the light along the pathway 74 is a mixture of light in the red and green wavelength spectra. This mixture of light from the pathway 74 is focused by the second optical lens 68 and transmitted along the pathway 76 to the second dichroic filter 52. Light in the blue wavelength spectrum is emitted by the first LED 32 along the pathway 78 toward the second optical component 32' and the second dichroic filter 52. Because the second dichroic filter 52 allows red and green light to pass and reflects blue light, the light along the pathway 80 is a mixture of blue, green, and red light. This light is transmitted along the pathway 80 and through optical lens 66, which focuses the light. The focused blue, green, and red light mixture is transmitted along the pathway 82 toward the first dichroic filter 50, which allows blue light, green light, red light to pass. Thus, all of the light transmitted along the pathway 82 passes through the first dichroic filter to an exit pathway 84. The mixture of blue light, green light, and red light, i.e. white light, is transmitted along the exit pathway 84 to the lens system 22, as shown in FIG. 4a.

Figure 4B:
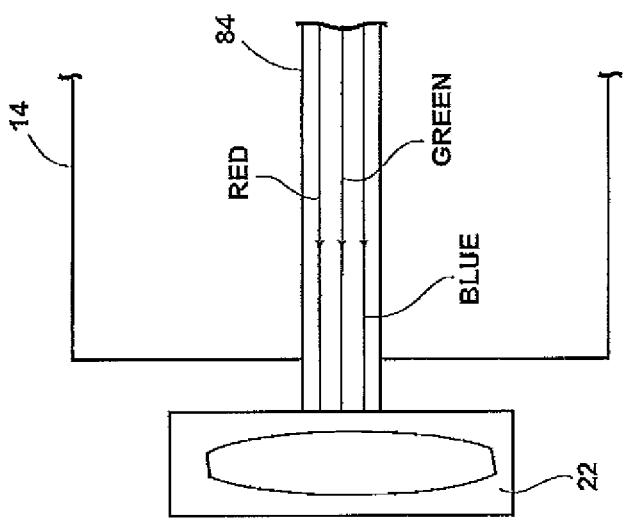
FIG. 4b is a diagrammatic view of a collimating lens receiving light of a second set of light wavelengths.

In the second mode, power is provided to the laser diode driver 38, to the first LED driver 40, and to the second LED driver 42, but is not provided to the third LED driver 44. Thus, the light source 14 provides infrared light (having a wavelength between 710 nm and 820 nm, but preferably having a wavelength of 808 nm), light in the blue wavelength spectrum, and light in the green wavelength spectrum. Because the third LED 36 provides no light in the second mode, there is no light transmitted along pathway 70. The second LED 34 emits light in the green wavelength spectrum along pathway 72 in the direction of the third optical component 34' and the third dichroic filter 54, which reflects the green light. As a result, the green light is transmitted along the pathway 74, to and through the optical lens 68, and along the pathway 76 to the second dichroic filter 52. Light in the blue wavelength spectrum is emitted by the first LED 32 along the pathway 78 in the direction of the second optical component 32' and the second dichroic filter 52. Because the second dichroic filter 52 passes light in the green wavelength spectrum and reflects light in the blue wavelength spectrum, a mixture of blue light and green light is transmitted along the pathway 80, to and through the optical lens 66, and along the pathway 82 to the first dichroic filter 50. The laser diode 30 emits 808-nm infrared light along a pathway 86 in the direction of the first optical component 30' and the first dichroic filter 50. Because the first dichroic filter passes light in the visible wavelength spectrum, and reflects 808-nm infrared light, the result of light transmitted along the exit pathway 84 is a mixture of 808-nm infrared light, green light, and blue light, as shown in FIG. 4b. This mixture of light is transmitted to the lens system 22.

After the light, either in the first mode or in the second mode, passes through the lens system 22, it is transmitted through the light pipe 24, through the fiber optic light guide 26, and to the endoscope 12 via the light post 28. The light transmits through the illumination pathway 12' of the endoscope to the object 1.

Figure 4C:
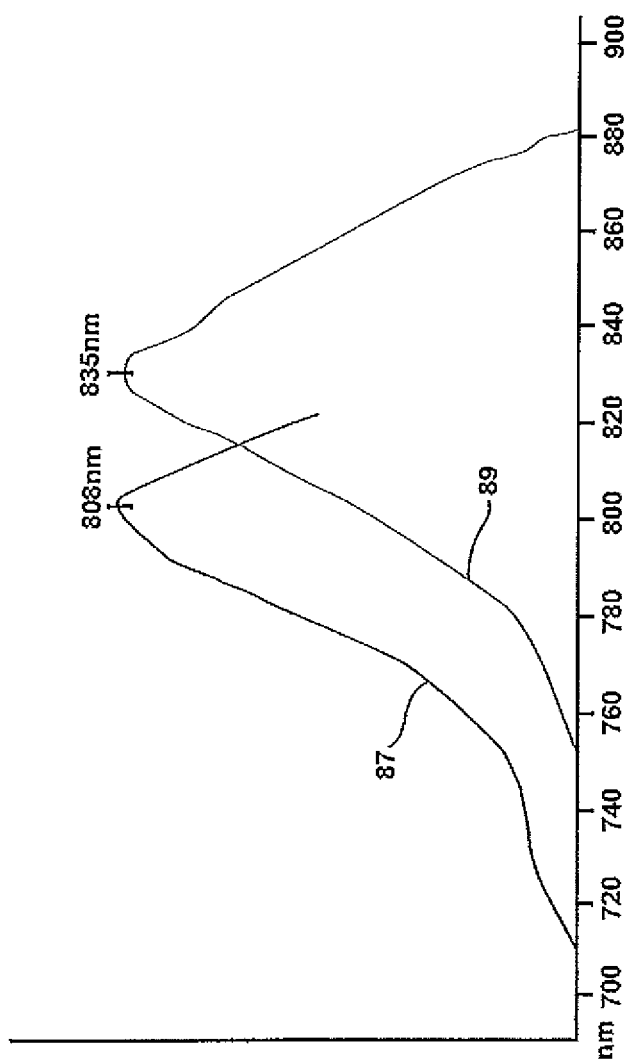
FIG. 4c is a graph showing an excitation light wavelength band and a marker emission light wavelength band.

In the first mode, visible light is reflected off of the object 1, a portion of which is received by the endoscope 12, and which is transmitted to the camera head 16 via the optical channel pathway 12". In the second mode, 808-nm infrared light, as well as light in the blue and green wavelength spectra, are transmitted to the object 1. The light in the blue and green wavelength spectra is reflected by the object 1, a portion of which is received by the endoscope 12. In addition, the 808-nm infrared light excites the fluorescent markers 2 in the object. The excitation of the fluorescent markers 2 causes the markers 2 to emit their own light, which is also in the infrared spectrum. The fluorescent marker light preferably has a wavelength between about 760 nm and about 880 nm, with the fluorescent marker light having a peak emission wavelength in the range of about 830 nm to about 840 nm, and more preferably about 835 nm. A graph of the excitation light wavelength band 87 and the fluorescent marker light wavelength band 89 is depicted in FIG. 4c. The excitation infrared light can be distinguished and/or separated from the fluorescent marker light, as discussed below. The emitted marker fluorescent light, and typically a portion of reflected 808-nm excitation light, is received by the endoscope 12. The blue light, green light, and infrared lights are transmitted to the notch filter 31, where 808-nm light is blocked. The unblocked light passes through the notch filter 31 and is transmitted to the camera head 16.

Figure 5:
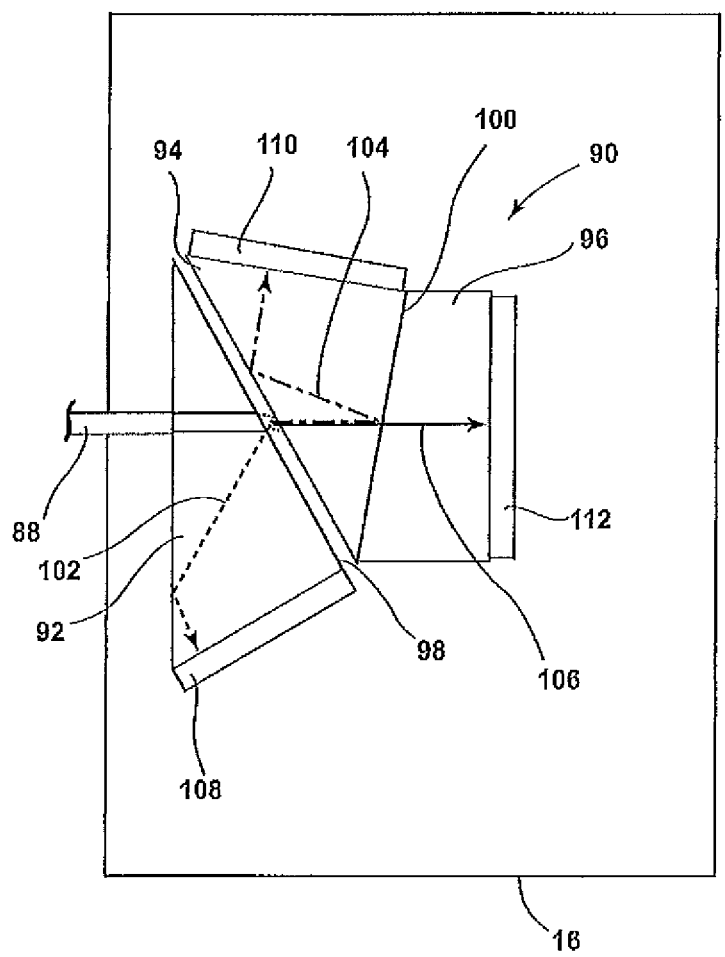
FIG. 5 is a diagrammatic view of an embodiment of a camera head of the present invention, which includes a trichroic prism for separation of light by wavelength, and image sensors for transformation of light to image signals.

The light, either in the first mode or in the second mode, returns along a path, depicted as part number 88 in FIG. 5, to the camera head 16. The camera head 16 includes, among other components not shown, a trichroic prism 90. The trichroic prism 90 includes a first glass prism 92, a second glass prism 94, and a third glass prism 96. Between the first glass prism 92 and the second glass prism 94 is a first prism filter 98, which may be in the form of a coating on the exterior of the first glass prism 92. The first prism filter 98 reflects blue light, but transmits other light, such as red light, green light, and infrared light. Between the second glass prism 94 and the third glass prism 96 is a second prism filter 100, which may be in the form of a coating on the second glass prism 94. The second prism filter 100 reflects red light and infrared light, but allows the transmission of light in other wavelengths, such as green light. Thus, blue light is transmitted along the pathway 102 as depicted in FIG. 5, red and infrared light are transmitted along the pathway 104, and green light is transmitted along the pathway 106.

A first color sensor 108 is adjacent, and preferably fixedly attached to, the first glass prism 92. A second color sensor 110 is adjacent, and preferably fixedly attached to, the second glass prism 94. A third color sensor 112 is adjacent, and preferably fixedly attached to, the third glass prism 96. The first color sensor 108 is capable of detecting light in the blue wavelength spectrum, the second color sensor 110 is capable of detecting light in the red and infrared wavelength spectra, and the third sensor 112 is capable of detecting light in the green wavelength spectrum. The color sensors 108, 110, 112 receive light and convert the light into electronic signals, which in turn are transmitted to the processor 18 for processing into analog or digital signals of images to be provided for display, such as to monitor 20.

In the first mode, visible light (red, green, blue) is sensed by the color sensors 108, 110, 112, and the resulting visible light signals are sent to the CCU 18, which in turn provides an image of the object 1 to the monitor 20 in full color. In the second mode, the sensors 108, 110, 112 provide signals to the CCU 18 representing a band of infrared light, green light, and blue light. The green light and blue light signals received by the CCU 18 are converted into a black and white image of the object 1 to create a background image. The infrared light signal is processed and sent to a visible "pseudo" color output, in this case the green output of the CCU 18 and to the monitor 20. Thus, in the second mode, the object 1 is presented as a black and white image, while the excited fluorescent markers 2 are displayed as green on the monitor 20.

The switching from the first (white light) mode to the second (IR) mode in both the light source 14 and the CCU 18 can be achieved by use of camera head buttons, a CCU processor 18 touch screen, a light source 14 touch screen, a wireless controller touch screen, a voice control or a foot pedal.

Figure 6:
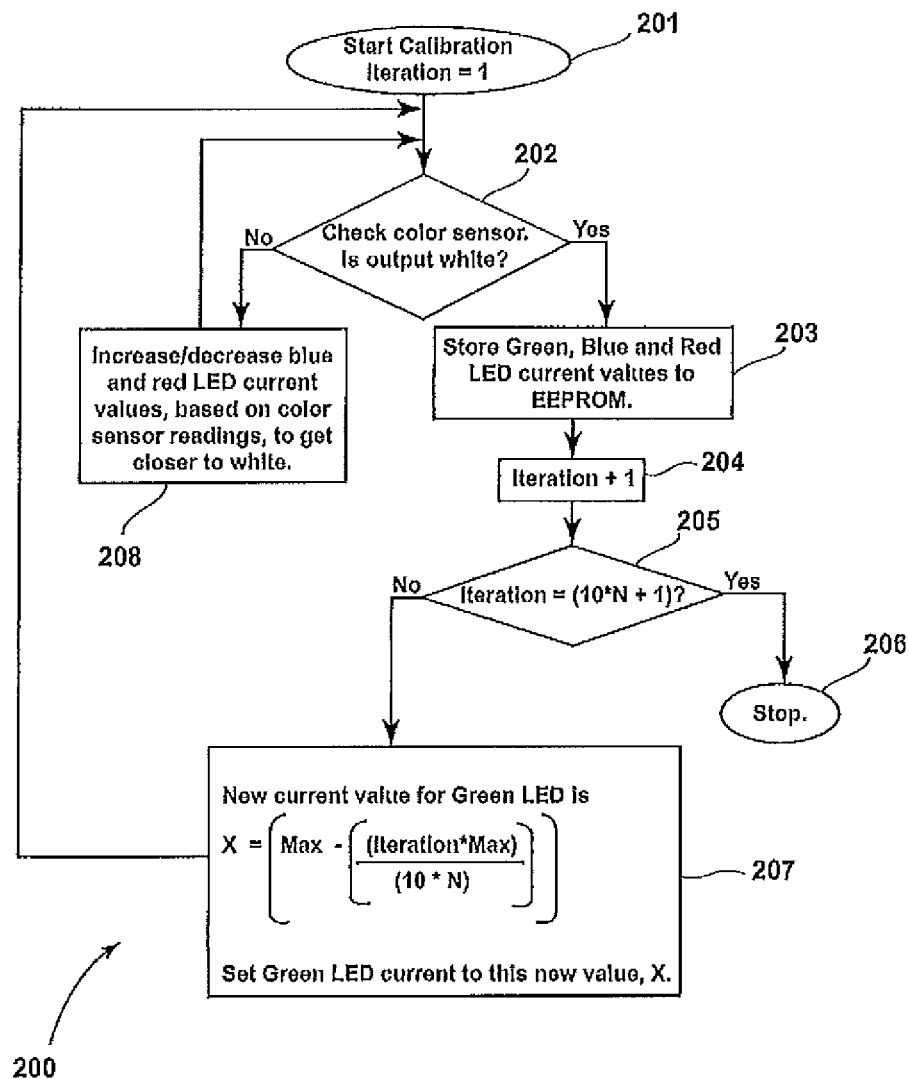
FIG. 6 is a flow chart of a color calibration routine.

The color balance circuitry/logic device 62 uses an algorithm routine 200 to calibrate the light output. The light source 14 is calibrated once in its life span. As shown in FIG. 6, calibration is started with a first iteration (201). The algorithm utilizes the color sensor 60 to measure the red, green, and blue light output from the LEDs 36, 34, 32, respectively, to determine whether the combination of red, green, and blue light creates white light. If white light is achieved, the LED current values of the red, green, and blue light are stored in a memory device such as an EEPROM, for the given intensity level (202).

In this system, there are 10 brightness levels available to the user, and the number of steps between the present brightness level and the next brightness level is designated as N. Accordingly, after storage of a white light current value, the iteration number is increased by 1 (204), and then the system determines if the iteration number equals 10*N+1 (205). If the iteration number equals 10*N+1, the routine is stopped (206). If not, the new current value for the green LED is set to X (207), with X being:

$$X = \text{Max} - \left(\frac{(\text{Iteration} * \text{Max})}{(10 * N)}\right)$$

The system then repeats the above process until the iteration number equals 10*N+1.

If the color sensor 60 does not detect white light at the start of the routine, the red and blue LED current values are increased or decreased, based on readings from the color sensor 60, to adjust the light to be closer to white light (208). The system then starts this portion of routine again to determine if the output is white light (202). The electrical currents supplied to the LEDs 32, 34, 36, are adjusted using a Digital-to-Analog Converter (DAC) 132 for the blue LED 32, a DAC 134 for the green LED 34, and a DAC 136 for the red LED 36.

Figure 7:
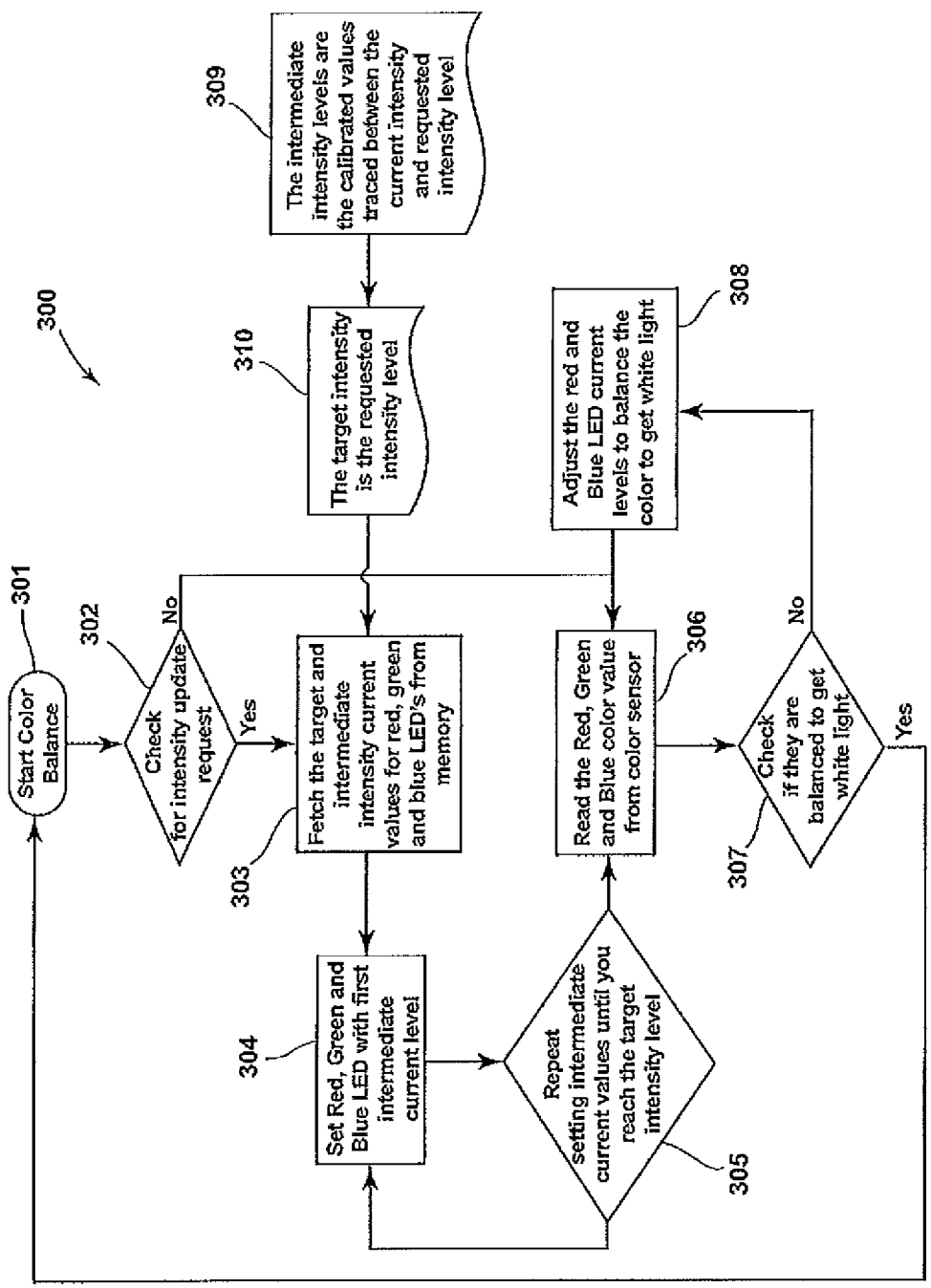
FIG. 7 is a flow chart of a color balance routine.

An algorithm routine for color balance is depicted diagrammatically in FIG. 7 and is designated generally as 300. The color balance feature is actively running whenever the unit is on. The color balance routine 300 achieves change in white light intensity without a significant, user-noticeable change in color of the light being output. The algorithm works such that when the color balance is started (301), it is determined whether the user has chosen a white light intensity level (302). If the user has chosen to change the intensity, the target intensity becomes the new, requested intensity (310). The system reads, from the EEPROM, intermediate (i.e., between the present intensity level and the target intensity level) intensity DAC current values for each LED 32, 34, 36, set at the time of calibration (309) to achieve white light for the new intermediate intensity level (303). Then the algorithm adjusts the DAC current values for all the LEDs in adjustments small enough so that the user cannot perceive the small deviations from white light in the color of the light being output (304). These adjustments are repeated until the DAC current values for each LED reach the calibrated DAC current values required for white light for the target intensity level (305).

At all times when the light source 14 is on and the algorithm 300 is not going through the change in light intensity portion of the routine (303, 304, 305), the system is color balancing. To do this, red light, green light, and blue light color values are determined by the color sensor 60 and forwarded to the color balance circuitry/logic device 62 (306). The device 62 determines whether the red, green, and blue lights are balanced to achieve white light (307). If the lights are not balanced to result in white light, the red and blue DAC current levels are adjusted relative to the green DAC current level. This process is then repeated until white light is achieved (308).

The light source 14 being able to communicate with the CCU 18 allows for the light source 14 to automatically change intensity of the white light, turn itself on or off, or change between the first (white light) mode and the second (IR) mode based on the state of the CCU 18. This is particularly useful when a user decides to change the specialty for which the endoscopic camera system 10 is being used. When the user changes the specialty on the CCU 18, the CCU 18 will automatically result in the light source 14 adjusting its brightness for that specialty.

Figure 8:
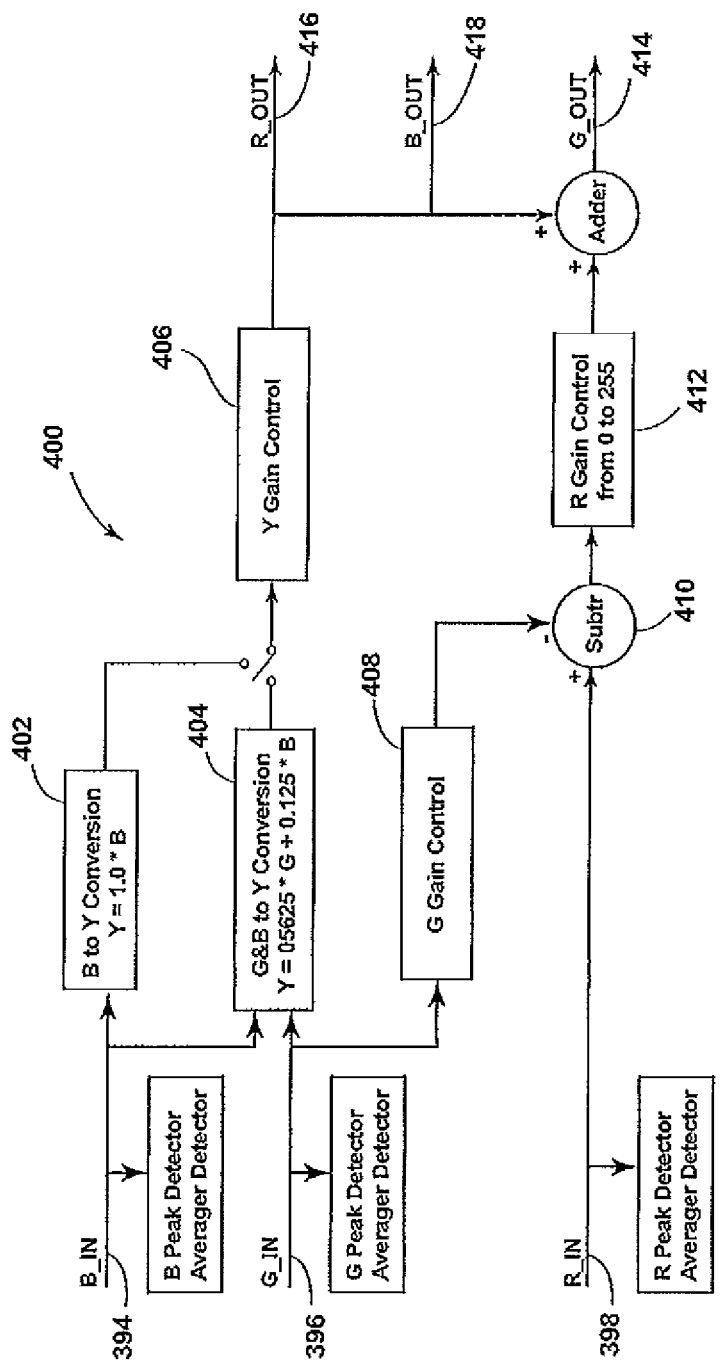
FIG. 8 is a flow chart of an infrared fluorescence routine.

FIG. 8 depicts an infrared fluorescence flow chart. When the light source 14, which is connected to the CCU 18, is switched to the second (IR) mode, an IRF algorithm routine 400 in the CCU 18 is activated. The IRF algorithm causes the following steps to occur. The system has a blue input channel 394, a green input channel 396, and a red input channel 398. Using the blue signal (B) from the blue input channel 394 and the green signal (G) from the green input channel 396, the luminance Y of B is calculated by using the formula Y=1.0*B (402), and/or the luminance Y of G and B combined is calculated by using the formula Y=0.5625*G+ 0.125*B (404). The luminance Y of B is calculated in the first (white light) mode and the luminance Y based on B and G is calculated in the second (IR) mode. A suitable luminance gain is then applied to the calculated luminance Y (406) and green input G (408) to enhance the input image.

The trichroic prism 90 is designed to have some overlapping of light spectra to ensure that the trichroic prism 90 does not favor one wavelength over another. Such overlapping, however, can cause some backlight to leak into the red sensor in the second, fluorescent mode. This leakage manifests itself by light in the green spectra leaking into the red sensor. Such leakage errors result in a smearing or portions of the resultant image which are "false." To account for this leakage, the current system includes an algorithm in the CCU to remove some amount of the green light green input value G from a red input value (R). The amount of green light removed from the red light is based on the value of the green input G (410).

A suitable red gain is also applied to the red input channel to enhance the image (412). In the second (IR) mode, the adjusted red channel value is then set to a green output channel 414 and the processed luminance Y is set to red and blue output channels 416, 418.

The described system allows for the traditional use of transmitted light to an object, such as a surgical site, through an endoscope with the reflected light being received and processed. In addition, the described system provides the advantage of providing infrared excitation light to the object for excitation of fluorescent markers. The endoscope is also capable of receiving both the reflected visible light and the excitation light from the object, which is in turn processed and provided as a display in an operating room. The described system uses no additional sensors or processors with respect to the previous white light only system.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. An endoscope system comprising:
   a light source comprising a first light device for emitting light in the red wavelength spectrum, a second light device for emitting light in the blue wavelength spectrum, a third light device for emitting light in the green wavelength spectrum, and a fourth light device for emitting infrared light, and a user operable switch for switching between a first light emission mode and a second light emission mode, wherein in the first light emission mode light in the red wavelength spectrum, light in the green wavelength spectrum and light in the blue wavelength spectrum are emitted and light in the infrared wavelength spectrum is not emitted, and in the second light emission mode light in the infrared wavelength spectrum, light in the green wavelength spectrum and light in the blue wavelength spectrum are emitted and light in the red wavelength spectrum is never emitted throughout the second light emission mode;
   an endoscope in communication with the light source, the endoscope being capable of receiving light from the light source and emitting the light onto a patient site and receiving reflected light and emitted fluorescent light from the patient site and transmitting the received light;
   a receiving device in communication with the endoscope and comprising a splitting filter capable of splitting a light mixture into separate wavelength rays, a first image sensor capable of detecting light in a green wavelength spectrum and converting the green light to a first image signal, a second image sensor capable of detecting light in a blue wavelength spectrum and converting the blue light to a second image signal, and a third image sensor capable of detecting light in a red wavelength spectrum and in an infrared wavelength spectrum and converting the red light and infrared light to a third image signal;
   a coupler for connecting the receiving device to the endoscope;
   a notch filter in the endoscope or coupler capable of blocking light of a specific wavelength range in the infrared spectrum and allowing other light in the infrared spectrum to pass therethrough; and
   a processor in electronic communication with the receiving device and disposed to receive the first image signal, the second image signal, and the third image signal, and to process the signals to create a display signal to be sent to a display apparatus.

2. The endoscope system of claim 1, wherein the first light device, the second light device, and the third light device are all light emitting diodes.

3. The endoscope system of claim 1, wherein the fourth light device is a laser diode.

4. The endoscope system of claim 1, wherein the emitted infrared light is at such a wavelength to excite fluorescent markers in an object.

5. The endoscope system of claim 1, wherein the receiving device is a camera.

6. The endoscope system of claim 1, wherein the splitting filter is a trichroic prism.

7. The endoscope system of claim 6, wherein the first image sensor, the second image sensor, and the third image sensor are all fixedly attached to the trichroic prism.

8. A method of using an endoscope system to view an object with fluorescent markers therein, the method comprising:
   providing a light source capable of emitting light in the red wavelength spectrum, emitting light in the blue wavelength spectrum, emitting light in the green wavelength spectrum, and emitting infrared light in a first infrared wavelength range, and a user operable switch for switching between a first light emission mode and a second light emission mode, wherein in the first light emission mode light in the red wavelength spectrum, light in the green wavelength spectrum and light in the blue wavelength spectrum are emitted and light in the infrared wavelength spectrum is not emitted, and in the second light emission mode light in the infrared wavelength spectrum, light in the green wavelength spectrum and light in the blue wavelength spectrum are emitted and light in the red wavelength spectrum is never emitted throughout the second light emission mode;
   providing an endoscope having a transmission light pathway in communication with the light source and a received light pathway, the transmission light pathway for transmitting light from the light source to the object and the received light pathway for receiving light from the object;
   providing a notch filter in communication with the endoscope;
   providing a first image sensor for receiving light in the red and infrared wavelength spectra, a second image sensor for receiving light in the green wavelength spectrum, and a third image sensor for receiving light in the blue wavelength spectrum;
   placing a fluorescent marker in or on the object which, when excited, emits light in a second infrared wavelength range;
   switching the light source to the second light emission mode to emit light to the object via the endoscope;
   the endoscope receiving light from the object;
   filtering the received light through the notch filter to block infrared light in the first infrared wavelength range;
   separating the received light into a first light in the infrared wavelength spectrum, a second light in the green wavelength spectrum, and a third light in the blue wavelength spectrum; and directing the first light to the first image sensor, directing the second light to the second image sensor, and directing the third light to the third image sensor.

9. The endoscope system of claim 1, wherein the notch filter allows at least 80% of infrared light not in the specific wavelength range to pass therethrough.

10. The endoscope system of claim 1, wherein the specific wavelength range is from 830 nm to 870 nm.

11. The endoscope system of claim 9, wherein the specific wavelength range is from 830 nm to 870 nm.

12. The endoscope system of claim 9, wherein the notch filter allows at least 80% of visible light in a wavelength range of 400 nm to 700 nm to pass therethrough.

13. The endoscope system of claim 1, wherein the notch filter has an optical density of OD5.

* * * * *